US010070233B2

(12) United States Patent
Westerkull

(10) Patent No.: US 10,070,233 B2
(45) Date of Patent: *Sep. 4, 2018

(54) IMPLANTABLE HEARING AID SYSTEM

(71) Applicant: MED-EL Elektromedizinische Geraete GmbH, Innsbruck (AT)

(72) Inventor: Patrik Westerkull, Askim (SE)

(73) Assignee: MED-EL Elektromedizinische Geraete GmbH, Innsbruck (AT)

(*) Notice: Subject to any disclaimer, the term of this patent is extended or adjusted under 35 U.S.C. 154(b) by 176 days.

This patent is subject to a terminal disclaimer.

(21) Appl. No.: 15/057,174

(22) Filed: Mar. 1, 2016

(65) Prior Publication Data

US 2016/0192092 A1 Jun. 30, 2016

Related U.S. Application Data

(63) Continuation-in-part of application No. PCT/US2014/046162, filed on Jul. 10, 2014, and a
(Continued)

(51) Int. Cl.
*H04R 25/02* (2006.01)
*H04R 25/00* (2006.01)
*A61N 1/36* (2006.01)

(52) U.S. Cl.
CPC ....... *H04R 25/606* (2013.01); *A61N 1/36032* (2013.01); *H04R 25/554* (2013.01);
(Continued)

(58) Field of Classification Search
CPC ................. H04R 25/02; H04R 25/60–25/608
(Continued)

(56) References Cited

U.S. PATENT DOCUMENTS

| 4,498,461 A | 2/1985 | Hakansson |
| 5,545,191 A | 8/1996 | Mann et al. |

(Continued)

FOREIGN PATENT DOCUMENTS

WO WO 00/00123 A1 1/2000

OTHER PUBLICATIONS

International Searching Authority, International Search Report—International Application No. PCT/US14/46162, dated Nov. 13, 2014, together with the Written Opinion of the International Searching Authority, 15 pages.

(Continued)

*Primary Examiner* — Catherine B Kuhlman
(74) *Attorney, Agent, or Firm* — Sunstein Kann Murphy & Timbers LLP

(57) ABSTRACT

An implantable hearing aid system is disclosed. The system has an external transmitter device and an implantable receiver device, and includes a skin interface to connect the external transmitter device to the head of a user. There is a transmitter connector on the external transmitter device and an interface connector on the skin interface to form a coupling between the skin interface and the external transmitter device to enable connection and disconnection of the external transmitter device to and from the skin interface. The skin interface has an adhesive surface facing the skin so that it can be adhered to the skin on the head of the user. The implantable receiver device has an implant stimulator to stimulate a hearing organ. Sound information is transmitted from the external transmitter device to the implantable receiver device that stimulates the hearing organ of the user.

20 Claims, 8 Drawing Sheets

Related U.S. Application Data continuation of application No. 14/017,593, filed on Sep. 4, 2013.

(52) U.S. Cl.
CPC ......... *H04R 25/65* (2013.01); *H04R 2225/67* (2013.01); *H04R 2460/13* (2013.01)

(58) Field of Classification Search
USPC .......................................................... 600/25
See application file for complete search history.

(56) References Cited

U.S. PATENT DOCUMENTS

| | | |
|---|---|---|
| 5,949,895 A | 9/1999 | Ball et al. |
| 6,275,737 B1 | 8/2001 | Mann |
| 2002/0019669 A1 | 2/2002 | Berrang et al. |
| 2002/0099421 A1 | 7/2002 | Goldsmith et al. |
| 2002/0120332 A1 | 8/2002 | Law et al. |
| 2005/0228214 A1 | 10/2005 | Schneider et al. |
| 2005/0249366 A1 | 11/2005 | Westerkull |
| 2012/0294466 A1 | 11/2012 | Kristo et al. |
| 2013/0089229 A1 | 4/2013 | Kristo et al. |
| 2013/0184804 A1 | 7/2013 | Dalton |

OTHER PUBLICATIONS

European Patent Office, Extended European Search Report, Application No. 14842972.3-1901, 9 pages, dated Feb. 27, 2017.

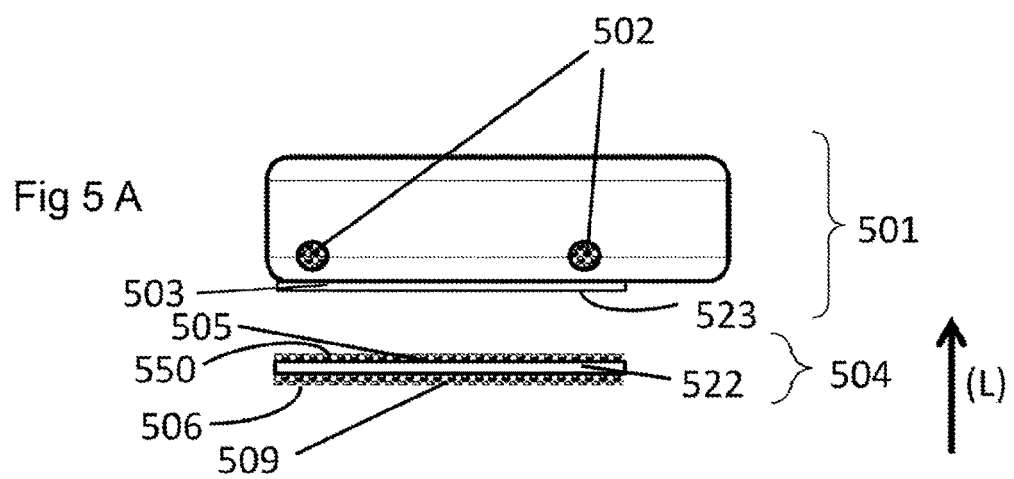
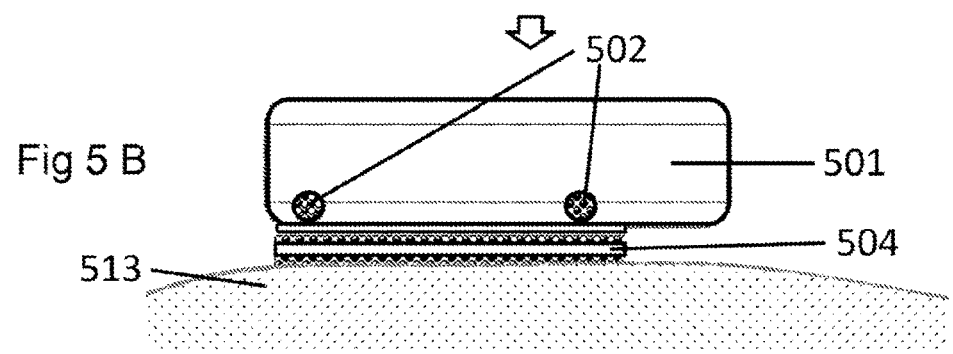

IMPLANTABLE HEARING AID SYSTEM

This application is a continuation-in-part of pending Patent Cooperation Treaty Application PCT/US2014/046162, filed Jul. 10, 2014, which in turn claims priority from U.S. patent application Ser. No. 14/017,593, filed Sep. 4, 2013, both of which are incorporated herein by reference in their entireties.

FIELD OF THE INVENTION

The present invention relates to a hearing aid system having an external transmitter device and an implantable receiver device, and wherein an implant communications signal with sound information is transmitted from the external transmitter device to the implantable receiver device that has an implant stimulator to stimulate the hearing organ.

BACKGROUND ART

Implantable hearing aid systems such as for example middle ear devices, implantable bone conductors and cochlear implants include an implanted receiver device that receives a signal from an external transmitter device via an inductive link. Both sound information and electrical energy are usually transmitted from the external transmitter device to the implanted receiver device via the inductive link. The implanted receiver device includes or is connected to an implant stimulator to stimulate the hearing organ. The implant stimulator may, for example, be a vibrator or an electrode array. For these types of implantable hearing aid systems, the external transmitter device is usually kept in place with a magnetic attachment, so there are magnetic materials in both the external transmitter device and in the implanted receiver device. These two units attract each other to keep the external transmitter device in position and retained on the head of the user.

A drawback of these systems is that the magnetic force presses the external transmitter device towards the skin which may cause skin irritation or even skin necrosis. The external transmitter device may also accidentally slide off from the patient's head quite easily. The efficiency of the inductive link is also quite poor since it is necessary to have a relatively thick skin between the implanted receiver and the external transmitter device to avoid skin necrosis due to the constant pressure against the skin. The magnetic material in the implanted receiver device may also hinder or complicate MRI (Magnetic Resonance Imaging) examinations of the user. In case of MRI examinations, the currently available implantable hearing aids usually require surgical removal of the magnet in the implanted receiver device.

To retain the external transmitter device on the head, it has of course been possible to attach an external transmitter device with tape or glue to the patients head but this has not been acceptable as a clinical solution due to, for example, drawbacks of using glue on the external transmitter device making it difficult to remove. Drawbacks of using tape over the external transmitter device include limited access to the external transmitter device as well as limited aesthetics.

There is a need for more effective implantable hearing aid systems that are reliable and do not have the drawbacks discussed above.

SUMMARY OF THE INVENTION

The present invention provides an effective solution to the above-outlined problems with implantable hearing aid systems such as middle ear devices, implantable bone conductors and cochlear implants. More particularly, the implantable hearing aid system of the present invention has a separate skin interface through which an external transmitter device is connected to the skin on the head of a user.

Embodiments of the present invention include an implantable hearing aid system, with an external transmitter device that has a transmitter housing with a transmitter connector. The transmitter housing contains a transmitter configured to transmit an implant communications signal. An implantable receiver device is configured for implantation under skin of a patient user. The implantable receiver device includes an implant receiver that is configured to receive the implant communications signal from the transmitter, and an implant stimulator that is coupled to the implant receiver and configured to produce an implant stimulation signal to stimulate a hearing organ of the patient user. A skin interface is configured to hold the external transmitter device over the skin over the implant receiver to couple the implant communications signal from the transmitter to the implant receiver. The skin interface includes opposing inner and outer interface surfaces, each having a front end and a rear end, wherein the front end is configured to be closer to an auricle of the patient user when the skin interface is attached to the patient user. An interface connector is located on the outer interface surface closer to the front end than to the read end and is detachably connectable to the transmitter connector for coupling the sound vibrations. A skin adhesive is located on the inner interface surface and is configured to adhesively connect to skin of the patient user. The skin adhesive is characterized by a surface texture that is configured so that when the skin adhesive is pressed against the skin of the user, the skin is initially engaged during an initial engagement period with an initial adhesive force that promotes removal and relocation of the skin interface, and the skin is fully engaged after the initial engagement period with a full adhesive force greater than the initial adhesive force that promotes a fixed secure connection that resists removal of the skin interface.

In further such embodiments, the surface texture is specifically characterized by structural peaks and valleys in the range of 0.1 mm to 1 mm. Embodiments may also include an implant magnet that is fixedly attached to the skull bone under the skin of the patient user, wherein the skin interface includes an external magnet configured to magnetically cooperate with the implant magnet for coupling the sound vibrations through the skin to the skull bone. The skin interface also may include at least one through hole extending between the inner and outer interface surfaces. The transmitter connector and the interface connector may possess a common center axis about which the transmitter housing is rotatable. And the transmitter connector may be tiltably detachable from the interface connector.

Embodiments of the present invention also include an implantable hearing aid system with an external transmitter device having a transmitter housing with a transmitter connector and containing a transmitter configured to transmit an implant communications signal. An implantable receiver device is configured for implantation under skin of a patient user, and includes an implant receiver configured to receive the implant communications signal from the transmitter, and an implant stimulator coupled to the implant receiver and configured to produce an implant stimulation signal to stimulate a hearing organ of patient user. A skin interface is configured to hold the external transmitter device over the skin over the implant receiver to couple the implant communications signal from the transmitter to the implant receiver. The skin interface includes rigid opposing inner and outer interface surfaces, each having a front end and a rear end, wherein the front end is configured to be closer to an auricle of the patient user when the skin interface is attached to the patient user. An interface connector is located on the rigid outer interface surface closer to the front end than to the read end and detachably connectable to the transmitter connector for coupling the sound vibrations. A skin adhesive is located on the rigid inner interface surface and configured to adhesively connect to skin of the patient user. And a cushioning layer is located in compliant engagement between the rigid inner interface surface and the skin adhesive to promote comfortable engagement of the hearing aid system with the skin of the patient user.

In further such embodiments, the rigid opposing inner and outer interface surfaces are surrounded by an outer ring of flexible material, and the cushioning layer may be made of the same flexible material as the outer ring. The rigid opposing inner and outer interface surfaces may be at least partially embedded within the cushioning layer.

There also may be an implant magnet fixedly attached to the skull bone under the skin of the patient user, wherein the skin interface includes an external magnet configured to magnetically cooperate with the implant magnet for coupling the sound vibrations through the skin to the skull bone. The skin interface may include at least one through hole extending between the inner and outer interface surfaces. The transmitter connector and the interface connector may possess a common center axis about which the transmitter housing is rotatable. And the transmitter connector may be tiltably detachable from the interface connector.

Embodiments of the present invention also include an implantable hearing aid system having an external transmitter device having a transmitter housing with a transmitter mass and a transmitter connector, and containing a transmitter configured to transmit an implant communications signal. An implantable receiver device is configured for implantation under skin of a patient user, and includes an implant receiver configured to receive the implant communications signal from the transmitter, and an implant stimulator coupled to the implant receiver and configured to produce an implant stimulation signal to stimulate a hearing organ of patient user. A skin interface with an interface mass is configured to hold the external transmitter device over the skin over the implant receiver to couple the implant communications signal from the transmitter to the implant receiver. The skin interface has opposing inner and outer interface surfaces, each having a front end and a rear end, wherein the front end is configured to be closer to an auricle of the patient user when the skin interface is attached to the patient user. An interface connector is located on the outer interface surface closer to the front end than to the read end and detachably connectable to the transmitter connector for coupling the sound vibrations. A skin adhesive is located on the inner interface surface and is configured to adhesively connect to skin of the patient user. And the transmitter mass is at least five times greater than the interface mass; for example, at least ten times greater than the interface mass.

There also may be an implant magnet fixedly attached to the skull bone under the skin of the patient user, wherein the skin interface includes an external magnet configured to magnetically cooperate with the implant magnet for coupling the sound vibrations through the skin to the skull bone. The skin interface may include at least one through hole extending between the inner and outer interface surfaces. The transmitter connector and the interface connector may possess a common center axis about which the transmitter housing is rotatable. And the transmitter connector may be tiltably detachable from the interface connector.

The skin adhesive may be a separately arranged adhesive sheet having an outer skin adhesive surface configured to be connectable to the inner interface surface of the skin interface, and an inner skin adhesive surface configured to, when in use, being connectable to the skin of the user of the bone conduction hearing device. This is an efficient way to manufacture the skin adhesive on the skin interface and may also enable changing a worn out skin adhesive.

BRIEF DESCRIPTION OF THE DRAWINGS

FIG. 5 A is a side view of the composition of a skin interface and an external transmitter device of an embodiment of the present invention.

FIG. 5B is a side view of the embodiment shown in FIG. 5A where the components have been attached to each other and the skin interface is adhesively attached to a skin of a user.

DETAILED DESCRIPTION OF SPECIFIC EMBODIMENTS

In prior art implantable hearing aid systems that include an externally attached transmitter device, it was assumed that an adhesively attached external transmitter device required an adhesive patch that extended over the external transmitter device so that the ends of the adhesive patch can be attached to the head. The prior art adhesive patch or band encloses the external transmitter device, and the adhesive is therefore attached directly to the top of the external transmitter device to hold the device in place on the head of the user. But by stretching the adhesive patch over the external transmitter device, the adhesive patch also provides an inwardly directed pressure onto the skin. The adhesive attachment area on the head of the user may then also have to be quite large.

The present invention is based on the realization that an adhesive can be located between the external transmitter device and the skin on a contact area that is directly applied to the skin to hold the external transmitter device in place in a bare area behind the ear without hair. Although little or no pressure is applied on the skin by the adhesive, implant communications signals from the external transmitter device are properly and effectively transmitted across the skin to the skull implant receiver. The fact that little or no pressure is applied on the skin, means the external transmitter device is more comfortable to wear for the user. In addition, the adherence is sufficiently strong so that the user can easily snap on and snap off the external transmitter device from the skin interface without tearing the skin interface off the skin. This makes it possible for the user to only attach the external transmitter device to the skin interface when necessary. and the user also can easily remove it without removing the skin interface when needed such as when sleeping or swimming.

Figure 1:
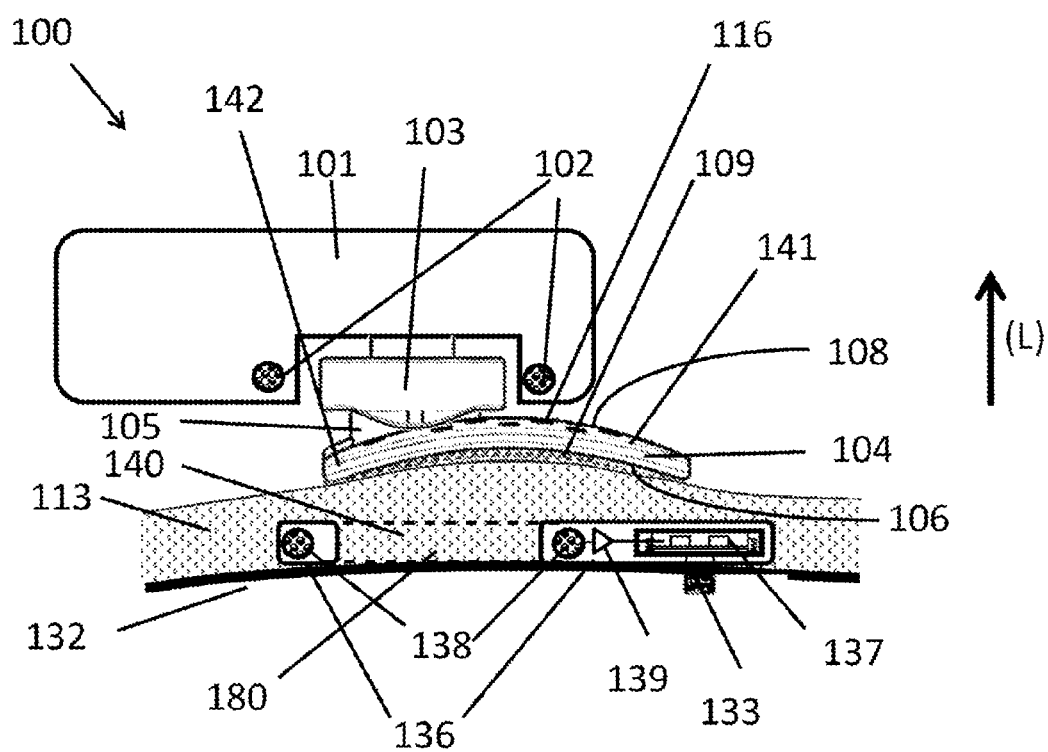
FIG. 1 is a side cross-sectional view of the implantable hearing aid system of the present invention attached to a skull bone of a user.

FIG. 1 is a side overview of the implantable hearing aid system 100 of the present invention. An external transmitter device 101 contains a transmitter including a transmitter coil 102 (shown as a cross-sectional view) configured to transmit an implant communications signal. The external transmitter device 101 also includes a transmitter housing with a transmitter connector 103 on its outer surface. A skin interface 104 has an outer interface surface 108 that faces the away from the skin toward the external transmitter device 101, and an inner interface surface (not marked) facing the skin opposite to the outer interface surface 108. The outer interface surface 108 has an interface connector 105. The transmitter connector 103 and the interface connector 105 form a mechanical coupling since they are detachably connectable to each other. The inner interface surface has a skin adhesive 109.

The lateral direction (L) has been marked. A contralateral direction may be a direction opposite to the lateral direction (L) and a lateral side of a component may be a side facing the lateral direction and a contralateral side may be facing a contra-lateral direction. The lateral direction (L) may be defined as the direction pointing out from or away from the patient's skin when the implantable hearing aid system 100 is connected to the skin of the patient. The outer interface surface 108 may, for example, be a lateral side of the skin interface 104, and the skin adhesive 109 has a second adhesive surface 106 at the contralateral side of the skin adhesive 109 so that the adhesive surface 106 faces a skin 113 of a patient user.

The adhesive surface 106 can be removably connected to the skin 113 on the head of a user and the transmitter connector 103 is removably connected to the interface connector 105 of the skin interface 104 by inserting a portion of the interface connector 103 into a cavity (not shown here) defined inside the interface connector 105. The external transmitter device 101 also may include a microphone (not shown) that picks up sound.

An implantable receiver device 136 includes an implant stimulator 137 that produces an implant stimulation signal to stimulate a hearing organ of the patient user. The implantable receiver device 136 is located under the skin 113 and it is fixated to a skull bone 132 with a fixation device 133. The implantable receiver device 136 also includes an implant receiver comprising a receiving induction coil 138 and a driver circuit 139 receives the implant communications signal from the transmitter 102 and outputs to the implant stimulator 137. The implantable receiver device 136 also has a through hole 140 defined therein through the center 180 of the receiving induction coil 138 to allow the skin 113 to grow through the hole 140 so that the skin 113 disposed under the adhesive skin interface 104 is further fixated to the underlying skull bone 132.

One useful feature of the present invention is that the patient or user may simply remove the external transmitter device 101 by snapping the transmitter connector 103 from the interface connector 105, and it may, preferably, require less force to remove the transmitter connector 103 from the interface connector 105 than does removing the skin adhesive 109 from the skin 113. In this way, the patient may easily remove the external transmitter device 101 from the skin interface 104 without inadvertently removing the skin interface 104 from the skin 113 of the patient. To promote this, the transmitter connector 103 can be disconnected from the interface connector 105 by tilting it in relation to the interface connector 105, thus generating significantly less pulling forces on the skin from the inner skin adhesive surface 106 when disconnecting the transmitter device 101 from the skin interface 104 that is adhesively attached to a user. To enable disconnecting the external transmitter device 101 from the skin interface 104 with a tilting force, the skin interface 104 is sufficiently rigid so that the skin interface 104 is not deformed or bent when applying a tilting force since such deformation or bending may prevent the intended disconnection of the external transmitter device 101 from the skin interface 104 by using the above described tilting force.

Specifically, the connection between the transmitter connector 103 and the interface connector 105 may have a female-male configuration such that the external transmitter device 101 cannot slide in a sideways direction relative to the skin interface 104, i.e. in a direction that is perpendicular to the lateral direction (L). The transmitter connector 103 may specifically be a substantially rigid female connection portion, and the interface connector 105 may specifically be a male connection portion that consists of flexible and elastic protruding spring arms so that the transmitter connector 103 can be snapped onto the interface connector 105. It is also possible to make the interface connector 105 rigid and the transmitter connector 103 flexible or elastic. When the transmitter connector 103 has been snapped onto the interface connector 105, the flexible interface connector 105 establishes a coupling force that keeps the external transmitter device 101 and the skin interface 104 together.

The transmitter connector 103 and the interface connector 105 may also include magnetic materials that adhere to one another so that the external transmitter device 101 is magnetically attached to the skin interface 104. If such magnets are used, the transmitter connector 103 and the interface connector 105 may be configured to have mechanisms to prevent sideways movement such as by using protruding parts that prevent sideways movement of the transmitter connector 103 relative to the interface connector 105.

The external transmitter device 101 may, in general, also include a microphone, electronics, battery and volume control which are not shown in the drawings, or the transmitter device 101 may be connected with a cord to another unit that includes battery, microphone etc. and/or a conventional audiometer for audiometry.

The skin interface 104 may include a plurality of through holes 116 defined therethrough so that air and moisture may be transported through the skin interface 104 to reach portions of the patient's skin that is below the inner skin adhesive surface 106. The through holes 116 allows for moisture and air transportation through the skin interface 104 which is beneficial to the skin to which the skin interface 104 is attached with the skin adhesive 109. In some embodiments, the skin interface 104 may have multiple through holes 116 defined therein and the skin interface 104 may also have a porous material for the same purpose.

The female transmitter connector 103 can be turned about the center axis of the coupling relative to the male interface connector 105 connected thereto. This is useful since it is then possible to adjust the orientation of the external transmitter device 101 when it is connected to the skin interface 104 attached to the user. There should be sufficient friction between the transmitter connector 103 and the interface connector 105 to provide that the external transmitter device 101 is still kept in an accurate position.

The outer interface surface 108 has a front end 141 and a rear end 142. The front end 141 is closer to the auricle of the user ear than the rear end 142 when the skin interface 104 is adhered to the skin behind the ear (best shown in FIG. 2). The interface connector 105 should be eccentrically positioned on the skin interface 104 so that the interface connector 105 is off-center and closer to or at the rear end 142. That positions the external transmitter device 101 further to the rear to avoid the external transmitter device 101 from touching the auricle of the user ear, preferably positioned on the naturally non-hair baring area behind the auricle since the adhesive attachment of the skin interface 104 would be less efficient on a hair baring area. Also not touching the auricle with the skin interface 104 avoids feedback and poor sound quality as well as discomfort.

The interface connector 105 may be an elastic plastic snapping device and the transmitter connector 103 may be a more durable female connection so that the wear is on the male interface connector 105, which is more frequently changed, instead of the wear being on the external transmitter device 101 which would need to be sent to repair when worn out. However, it is also possible to design the transmitter connector 103 and the interface connector 105 so that the latter is more wear resistant than the former, and so that the female interface connector 105 is more flexible and elastic compared to the male transmitter connector 103. To achieve a stable and durable coupling, both the transmitter connector 103 and the interface connector 105 include some substantially rigid mechanical components.

Figure 2:
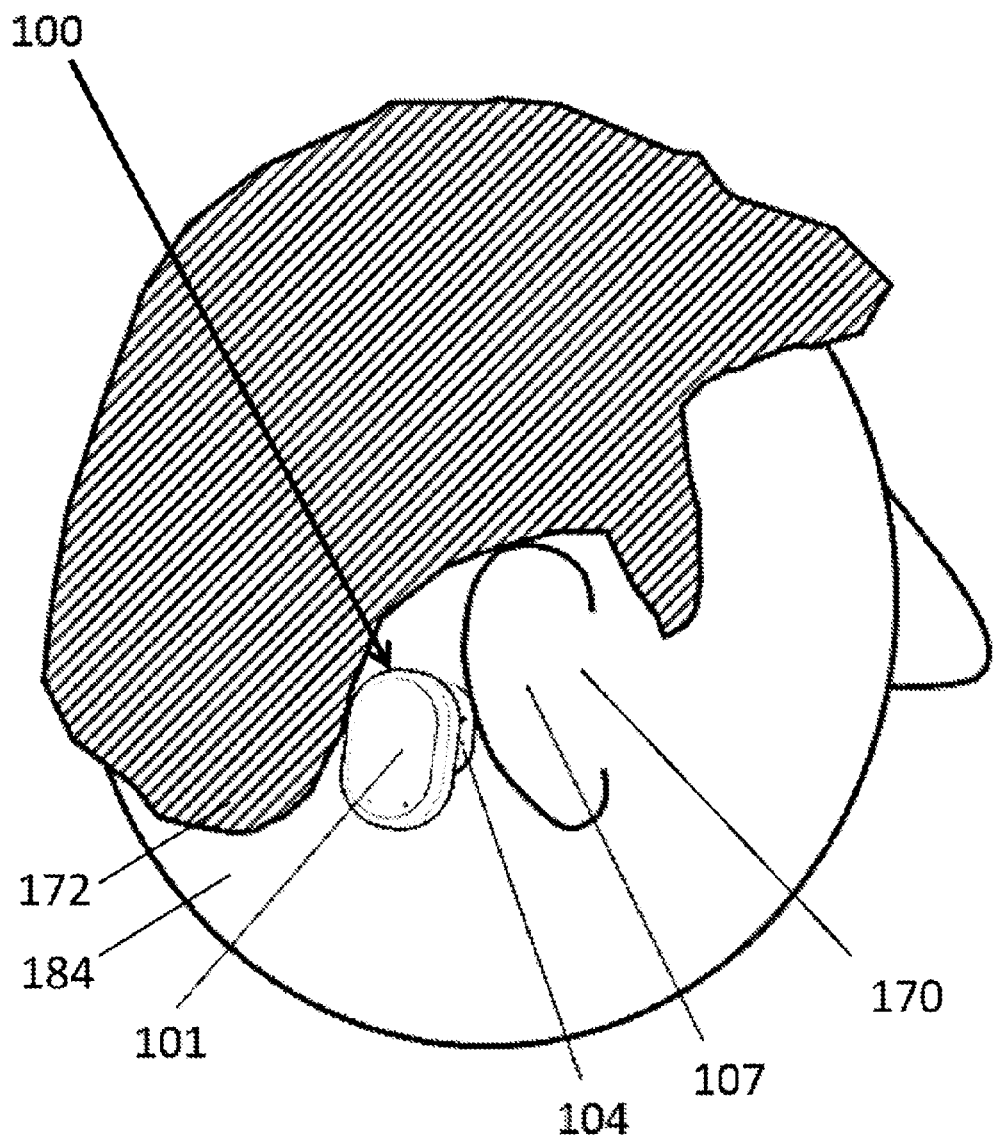
FIG. 2 is a perspective side view of the implantable hearing aid system of the present invention.

FIG. 2 is a perspective side overview of the implantable hearing aid system 100 of the present invention when it is in position on and attached to the head 184 of a user 172. The external transmitter device 101 is connected to the skin interface 104 which is connected with an adhesive surface to the skin behind the ear 107 of the user 172. Sound information and energy may be transmitted from the external transmitter device 101 to the implantable receiver device (not shown here) under the skin so that the implantable receiver device can stimulate the hearing organ 170 of the user 172.

Figure 3A:
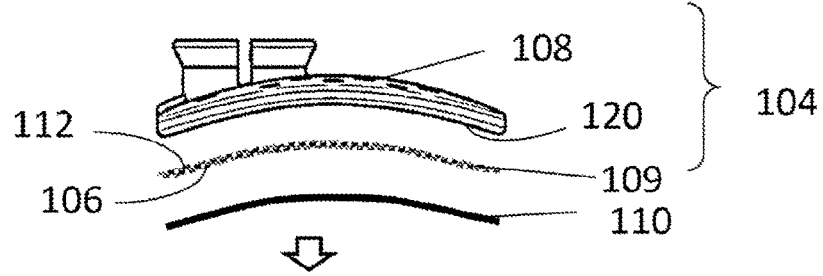
FIG. 3A is a side view of the skin interface of the present invention with a skin adhesive and protective part separated from the skin interface.

FIGS. 3A-3D are side views of the composition (FIG. 3A and FIG. 3B) and the application (FIG. 3C and FIG. 3D) of the skin interface 104 of the implantable hearing aid system of the present invention. A lateral direction (L) has been marked. In FIG. 3A the following separated parts are shown before assembly in manufacturing: the skin interface 104 has an outer interface surface 108, an inner interface surface 120 and an adhesive surface 109 that may be a double-sided adhesive sheet, and a protective sheet 110 that is useful to protect a contralateral skin adhesive 106 of the adhesive surface 109 during transportation and also prevents the adhesive from attaching to the skin of a user when trying out a suitable curvature version of the skin interface 104 for a specific user. The protective sheet 110 may be a polymer sheet.

A user friendly feature is that the skin adhesive 109 (such as a double-sided adhesive sheet) is adapted to be applied to the skin and that it allows oxygen to penetrate therethrough.

It is also possible for the user to remove the skin interface 104 completely, for example, during a night so that the skin is not permanently interfered with and can "breathe" and function normally when the patient does not need to use the implantable hearing aid system 100. It may also be possible to configure the skin adhesive 109 as an adhesive material, such as glue, that is directly applied to the inner interface surface 120 instead of configuring it as a double-side adhesive sheet. However, the use of a double-sided adhesive sheet may be efficient in manufacturing when applying a contralateral skin adhesive 109 to the inner interface surface 120. The skin adhesive 109 has an outer skin adhesive surface 112 facing the inner interface surface 120. Instead of using an adhesive on the outer skin adhesive surface 112, it is also possible to use other removable attachment mechanisms such as Velcro or separate glue. Since the skin adhesive 109 may be removably attached to the inner interface surface 120, it is also possible to change the sheet of the skin adhesive 109 if this is more cost efficient than to take a complete new skin interface 104 that includes a new skin adhesive 109.

Figure 3B:
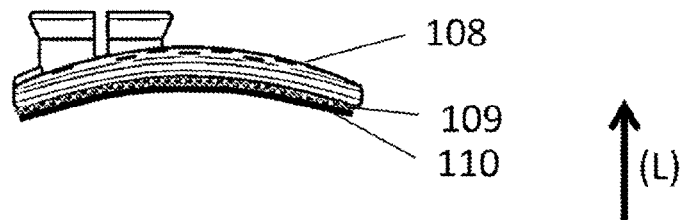
FIG. 3B is a side view of the embodiment shown in FIG. 3A with the skin adhesive and protective part attached to the skin interface.
Figure 3C:
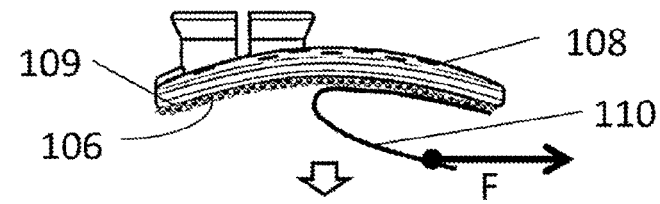
FIG. 3C is a side view of the embodiment shown in FIG. 3B with the protective part partially removed.
Figure 3D:
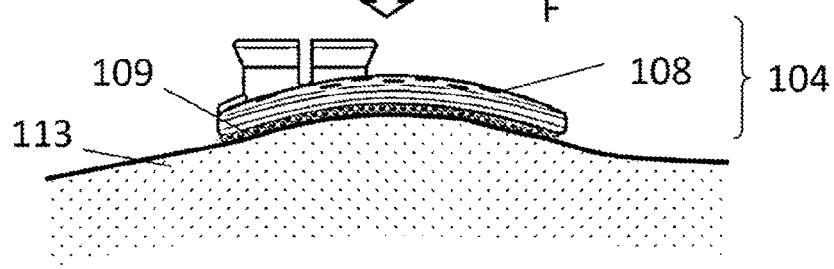
FIG. 3D is a side view of the embodiment shown in FIG. 3C with the protective part fully removed and the embodiment attached to a skin portion of a user.

In FIG. 3B, the parts shown in FIG. 3A have been assembled so that the double-sided sheet of the skin adhesive 109 has been adhered to the inner interface surface 120, and the protective sheet 110 has been attached to the inner skin adhesive surface 106 so that the entire unit is ready for transportation. In FIG. 3C, the protective sheet 110 is removed from the inner skin adhesive surface 106 by applying a force (F) to expose the contralateral inner skin adhesive surface 106. In FIG. 3D, the skin interface 104 with its double-sided sheet skin adhesive 109 has been adhesively attached to the skin 113 on the head of a user.

Figure 6:
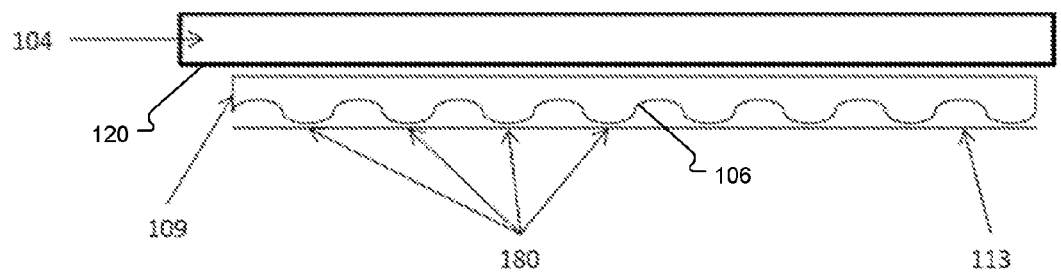
FIG. 6 is a close up view of a section of the adhesive surface according to an embodiment of the present invention

When attached to the skin interface 104, the inner skin adhesive surface 106 of the skin adhesive 109 facing the skin 113 may have an uneven surface texture as shown in FIG. 6 in the scale of 0.1 mm to 1 mm between peaks and valleys. This uneven surface texture may have the advantage that during an initial engagement period immediately after placing the inner skin adhesive surface 106 on the skin 113, there is only contact between the protruding portions 180 of the skin adhesive 109 and the skin 113. Therefore, during the initial engagement period, there is a reduced initial adhesive force which allows the skin interface 104 to be relatively easily removed and relocated, if e.g. the placement needs to be changed to optimize it for the user. After the initial engagement period, e.g. a couple of minutes to half an hour, more of the adhesive material in the skin adhesive 109 is in contact with the skin 113 due to the viscosity and tackiness of the adhesive, thus increasing the adhesive contact area between the skin interface 104 and the skin 113, resulting in relatively stronger full adhesive force between the skin interface 104 and the skin 113 that promotes a fixed secure connection that resists (unintentional) removal of the skin adhesive 109.

Figure 4:
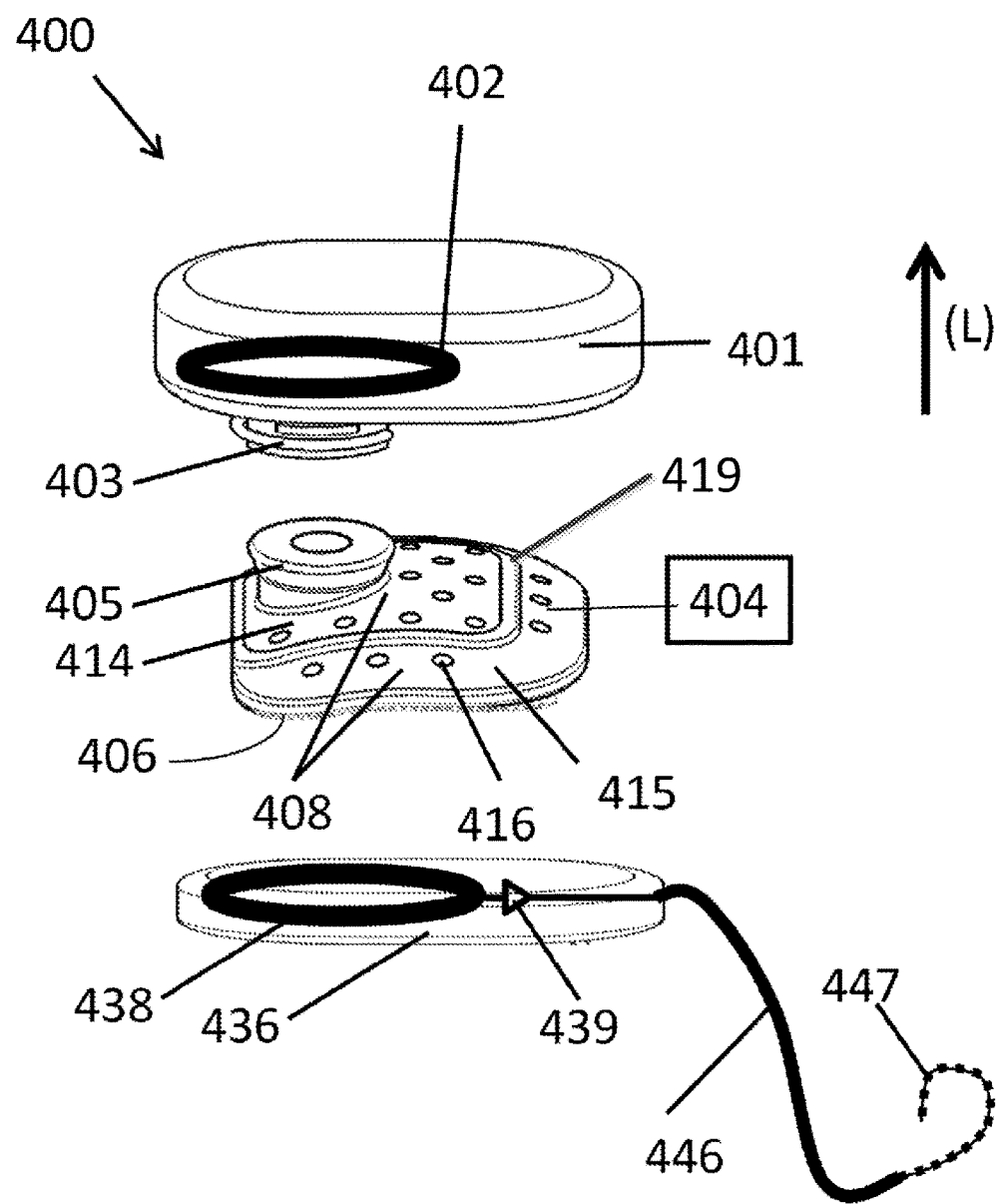
FIG. 4 is a perspective side view of an embodiment of the implantable hearing aid system of the present invention.

FIG. 4 is a perspective side view of the implantable hearing aid system 400 of the present invention. An external transmitter device 401 has a transmitter connector 403. A skin interface 404 has an outer interface surface 408 with a conical-shaped interface connector 405 and an adhesive surface 406 on its contralateral side. The transmitter connector 403 is a female coupling that has a flexible portion and a recess defined therein. The interface connector 405 may be a rigid male coupling so that the flexible female coupling of the transmitter connector 403 can be snapped onto the male interface connector 405. Similar to the embodiment described above the connectors could be reversed so that the transmitter connector 403 is a male connector and the interface connector 405 is a female connector.

Because an inner diameter of the recess of the flexible female transmitter connector 403 is slightly smaller than an outer diameter of the male interface connector 405, the transmitter connector 403 generates a coupling force about the interface connector 405 that keeps the external transmitter device 401 and the skin interface 404 together. The transmitter connector 403 also acts as a member around the protruding interface connector 405 that hinders the external transmitter device 401 from sliding off the skin interface 404 in a sideways direction (i.e. a direction perpendicular to a the lateral direction (L)).

The skin adhesive 406 on the contra-lateral side of the skin interface 404 is preferably attached to a skin surface behind the auricle of the user ear (best shown in FIG. 2). The outer interface surface 408 has a rigid inner portion 414 and a softer flexible and bendable peripheral outer ring 415 to facilitate adhesion of the skin adhesive 406 to various curvature skin surfaces. Because the rigid inner portion 414 is sufficiently rigid, it makes it easier for the user to separate the housing connector 403 from the interface connector 405, especially when disconnecting, so that the hearing aid device 401 is tilted in relation to the skin interface 404. It is helpful for the wearing comfort of the user that there is a soft cushioning layer 419 between the rigid inner portion 414 and the skin adhesive 406. This cushioning layer 419 may be made of the same material as the softer flexible and bendable peripheral outer ring 415. The rigid inner portion 414 may be attached to the surface of this soft cushioning layer 419, or it may be partially embedded in the cushioning layer 419. The skin interface 404 include multiple through holes 416 for air and moisture transportation to and from the skin through the skin interface 404. The external transmitter device 401 has a transmitter coil 402 that has been visualized therein. The implantable hearing aid system 400 has an implantable receiver unit 436 that includes a receiving coil 438 to receive sound information and energy from the transmitter coil 402. The implantable receiver device 436 includes processor electronics 439 and a cable 446 to a cochlear implant electrode 447 intended to be positioned in the cochlea of a user to provide cochlear implant hearing stimulation.

FIGS. 5A and 5B show side views of the composition (5A) and the application (5B) of parts of an implantable hearing aid system according to an embodiment of the present invention. Specifically, in FIG. 5A, an external transmitter device 501 and a skin interface 504 are shown when the external transmitter device 501 is not connected to the skin interface 504. The lateral direction (L) has been marked. A transmitter connector 503 is located at the contralateral side of the external transmitter device 501. The skin interface 504 comprises a double-sided adhesive-sheet with a carrier sheet 522, and an interface connector 505 is a first skin adhesive with a first adhesive surface 550 facing the external transmitter device 501. The skin interface 504 also has a second skin adhesive 509 at the opposite side of the carrier sheet 522 from where the interface connector 505 is located. The second skin adhesive 509 has an adhesive surface 506 facing an opposite direction than the first adhesive surface 550. The first adhesive 550 can be connected to a contra lateral surface 523 of the transmitter connection portion 503.

In FIG. 5B, the adhesive surface 506 has been attached to a skin 513 of a user and the external transmitter device 501 has been adhesively connected to the adhesive connection portion 505. The external transmitter device 501 has a transmitter 502 to transmit a signal or energy to an implanted receiver device (not shown here). When the external transmitter device 501 is removed from the head of the user the skin interface 504 is also removed. The skin interface 504 may then be torn off from the surface 523 and replaced with a new skin interface 504 so that the adhesion to the skin 513 is sufficiently strong when attaching the external transmitter device 501 and the skin interface 504 to the head again. The external transmitter device 501 and the transmitter connector 503 may include through holes defined therethrough to allow air and moist transportation to and from the skin 113. The adhesive sheet 522 as well as the skin adhesives may also allow air and moist transportation to and from the skin.

The external transmitter device may include digital processing, directional microphones, noise reduction, feedback suppression and other electronic and software features that are beneficial and used in any type of regular or implantable hearing aids. The external transmitter device may consist of one housing unit where all electronics are included or it may consist of two or more separate housing units where different parts of the electronics are included in the different housings and where the separate housing units communicate with each other via wire or through wireless communication.

Figure 7:
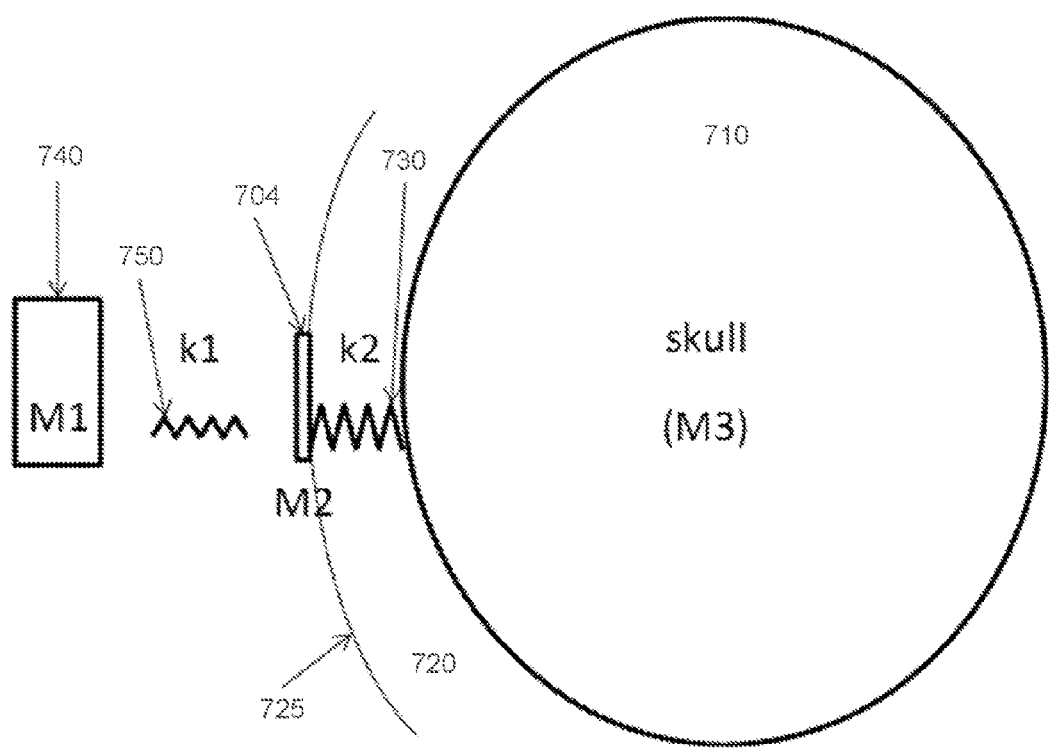
FIG. 7 shows the spring constant relationships that are present in various embodiments of the present invention.

Embodiments of the present invention provide a unique design of an integrated skin interface that enables the skin interface to be manufactured so that it has a very low weight in relation to the weight of the oscillating mass of the hearing aid device which is a key factor to achieve an efficient transmission of the vibrations from the hearing aid to the skull bone of a user. In specific embodiments of the present invention, as illustrated by FIG. 7, the mass ratio between the hearing aid device and the skin interface is a critical number. Unlike in percutaneous hearing implant systems that have a fixed connection between an abutment and the skull bone, here there is soft tissue 720 (e.g. skin 725, fatty tissue, etc.) between the (supercutaneous) skin interface 704 and the underlying skull bone 710 (represented by mass M3 in FIG. 7). This soft tissue 720 acts a sort of spring element 730 with a quasi-spring constant k2. The connection between a hearing aid device 740 (having mass M1) and skin interface 704 (having mass M2) can be thought of as a spring 750 having a spring constant k1. In specific embodiments, the mass ratio between the hearing aid device 740 and the skin interface 704 should be at least 5:1, preferably greater than 10:1.

Figure 8:
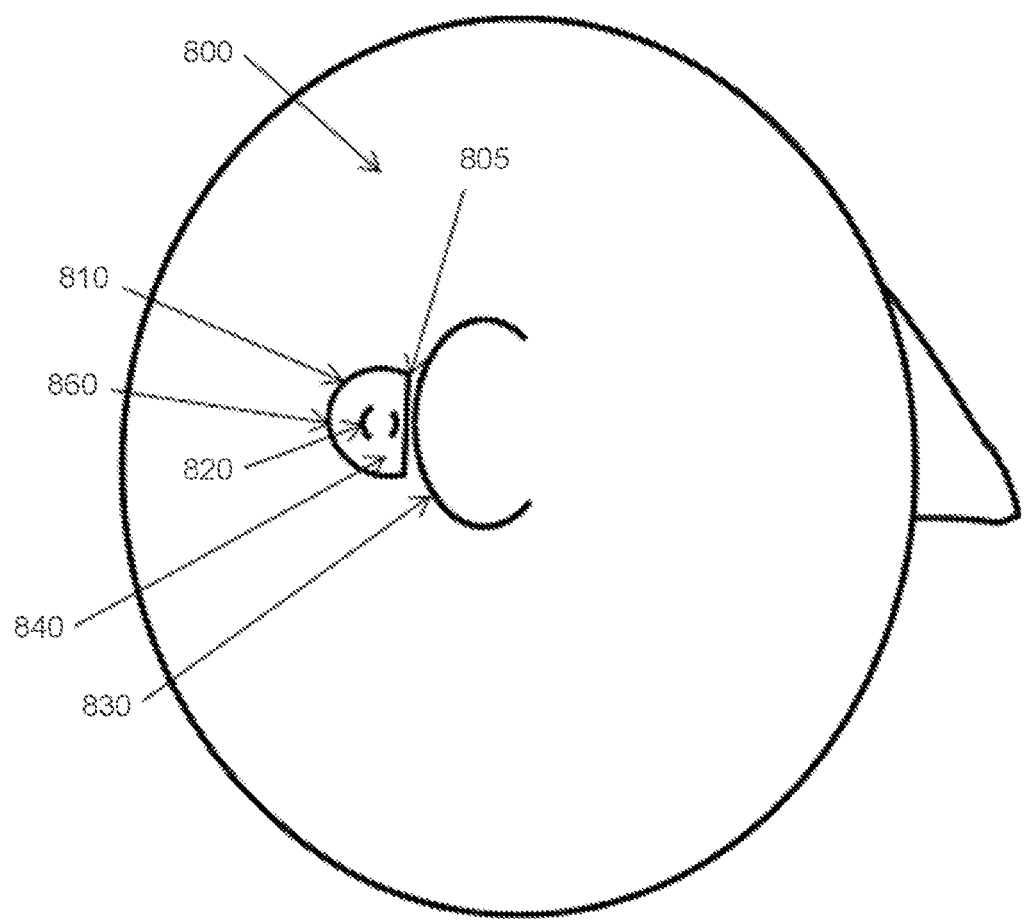
FIG. 8 shows the center of mass and asymmetric characteristics according to an embodiment of the present invention.

FIG. 8 shows a side view of a specific embodiment with a user 800 wearing a hearing aid device 810 having a skin interface (indicated by dashed circle) 820 behind the auricle 830. The hearing aid device 810 has an upper surface 840 which is asymmetric and has a geometrical center of mass that is, when worn by the user 800, closer to the front edge 850 that is placed nearest to the auricle 830, than to an opposite rear edge 860. In addition, the transmitter connector and interface connector consequently also are closer to the front edge 850 than to the rear edge 860 if they substantially coincide with this geometrical center of mass (as is generally the case). In a further specific embodiment, the mass distribution of the entire hearing aid system has a center of mass which may substantially lie on a line defined by the center axis of the two connectors. If the connectors are cylindrical, then this line coincides with the longitudinal cylindrical axis of the connectors. Similar types of axes can be defined if the shapes of the connectors are triangular, quadrilateral, oval annulus, etc. Consequently, the center of mass may be closer to the front edge 850 than to the rear edge 860. In particular, the center of mass may be close to the auricle 830. However, at the same time the hearing aid device 810 should not be in direct contact (should not touch) the auricle 830 itself to avoid undesired vibrational feedback.

The present invention has several advantages and may allow an external transmitter device to be retained on the user with an adhesive still allowing the user to take the external transmitter device on and off without having to tear the adhesive off the skin. The implant stimulator of the implantable receiver device may, for example, be a middle ear vibrator or a vibrator for generating bone conduction vibrations. The implant stimulator of the implantable receiver device may also be a cochlear implant electrode array positioned in the cochlea. The implantable receiver device may consist of more than one unit with cables extending between different units to optimize the positioning of the different parts of the implantable receiver device.

As described above, the implantable hearing aid system of the present invention includes a unique combination of technologies and provides new solutions and several advantages to meet complex user requirements. For all of the above embodiments several alternative designs and combinations are possible and the invention is not limited to the preferred embodiments presented above. While the present invention has been described in accordance with preferred compositions and embodiments, it is to be understood that certain substitutions and alterations may be made thereto without departing from the spirit and scope of the following claims.

Although various exemplary embodiments of the invention have been disclosed, it should be apparent to those skilled in the art that various changes and modifications can be made which will achieve some of the advantages of the invention without departing from the true scope of the invention.

What is claimed is:

1. An implantable hearing aid system, comprising,
an external transmitter device having a transmitter housing with a transmitter connector and containing a transmitter configured to transmit an implant communications signal;
an implantable receiver device configured for implantation under skin of a patient user, and including:
   i. an implant receiver configured to receive the implant communications signal from the transmitter, and
   ii. an implant stimulator coupled to the implant receiver and configured to produce an implant stimulation signal to stimulate a hearing organ of the patient user; and
a skin interface configured to hold the external transmitter device over the skin over the implant receiver to couple the implant communications signal from the transmitter to the implant receiver, the skin interface comprising:
   i. opposing inner and outer interface surfaces, and a front end and a rear end, wherein the front end is configured to be closer to an auricle of the patient user when the skin interface is attached to the patient user,
   ii. an interface connector on the outer interface surface closer to the rear end than to the front end and detachably connectable to the transmitter connector, and
   iii. a skin adhesive on the inner interface surface configured to adhesively connect to skin of the patient user;
wherein the skin adhesive is characterized by a surface texture configured so that when the skin adhesive is pressed against the skin of the user:
   i. the skin is initially engaged during an initial engagement period with an initial adhesive force that is configured to allow removal and relocation of the skin interface, and
   ii. the skin is fully engaged after the initial engagement period with a full adhesive force greater than the initial adhesive force that promotes a fixed secure connection that resists removal of the skin interface.

2. The implantable hearing aid system according to claim 1, wherein the surface texture is characterized by structural peaks and valleys in the range of 0.1 mm to 1 mm.

3. The implantable hearing aid system according to claim 1, wherein the transmitter connector and the interface connector include magnetic materials that adhere to each other so that the external transmitter device is magnetically attached to the skin interface.

4. The implantable hearing aid system according to claim 1, wherein the skin interface includes at least one through hole extending between the inner and outer interface surfaces.

5. The implantable hearing aid system according to claim 1, wherein the transmitter connector and the interface connector possess a common center axis about which the transmitter housing is rotatable.

6. The implantable hearing aid system according to claim 1, wherein the transmitter connector is tiltably detachable from the interface connector.

7. An implantable hearing aid system, comprising,
an external transmitter device having a transmitter housing with a transmitter connector and containing a transmitter configured to transmit an implant communications signal;
an implantable receiver device configured for implantation under skin of a patient user, and including:
   i. an implant receiver configured to receive the implant communications signal from the transmitter, and
   ii. an implant stimulator coupled to the implant receiver and configured to produce an implant stimulation signal to stimulate a hearing organ of the patient user; and
a skin interface configured to hold the external transmitter device over the skin over the implant receiver to couple the implant communications signal from the transmitter to the implant receiver, the skin interface comprising:
   i. rigid opposing inner and outer interface surfaces, and a front end and a rear end, wherein the front end is configured to be closer to an auricle of the patient user when the skin interface is attached to the patient user,
   ii. an interface connector on the rigid outer interface surface closer to the rear end than to the front end and detachably connectable to the transmitter connector,
   iii. a skin adhesive on the rigid inner interface surface configured to adhesively connect to skin of the patient user, and
   iv. a cushioning layer in compliant engagement between the rigid inner interface surface and the skin adhesive to promote comfortable engagement of the hearing aid system with the skin of the patient user.

8. The implantable hearing aid system according to claim 7, wherein the rigid opposing inner and outer interface surfaces are surrounded by an outer ring of flexible material.

9. The implantable hearing aid system according to claim 8, wherein the cushioning layer is made of the same flexible material as the outer ring.

10. The implantable hearing aid system according to claim 7, wherein the rigid opposing inner and outer interface surfaces are at least partially embedded within the cushioning layer.

11. The implantable hearing aid system according to claim 7, wherein the transmitter connector and the interface connector include magnetic materials that adhere to each other so that the external transmitter device is magnetically attached to the skin interface.

12. The implantable hearing aid system according to claim 7, wherein the skin interface includes at least one through hole extending between the inner and outer interface surfaces.

13. The implantable hearing aid system according to claim 7, wherein the transmitter connector and the interface connector possess a common center axis about which the transmitter housing is rotatable.

14. The implantable hearing aid system according to claim 7, wherein the transmitter connector is tiltably detachable from the interface connector.

15. An implantable hearing aid system, comprising,
an external transmitter device having a transmitter housing with a transmitter mass and a transmitter connector, and containing a transmitter configured to transmit an implant communications signal;
an implantable receiver device configured for implantation under skin of a patient user, and including:
  i. an implant receiver configured to receive the implant communications signal from the transmitter, and
  ii. an implant stimulator coupled to the implant receiver and configured to produce an implant stimulation signal to stimulate a hearing organ of the patient user; and
a skin interface with an interface mass configured to hold the external transmitter device over the skin over the implant receiver to couple the implant communications signal from the transmitter to the implant receiver, the skin interface comprising:
  i. opposing inner and outer interface surfaces, and a front end and a rear end, wherein the front end is configured to be closer to an auricle of the patient user when the skin interface is attached to the patient user,
  ii. an interface connector on the outer interface surface closer to the rear end than to the front end and detachably connectable to the transmitter connector, and
  iii. a skin adhesive on the inner interface surface configured to adhesively connect to skin of the patient user;
wherein the transmitter mass is at least five times greater than the interface mass.

16. The implantable hearing aid system according to claim 15, wherein the transmitter mass is at least ten times greater than the interface mass.

17. The implantable hearing aid system according to claim 15, wherein the transmitter connector and the interface connector include magnetic materials that adhere to each other so that the external transmitter device is magnetically attached to the skin interface.

18. The implantable hearing aid system according to claim 15, wherein the skin interface includes at least one through hole extending between the inner and outer interface surfaces.

19. The implantable hearing aid system according to claim 15, wherein the transmitter connector and the interface connector possess a common center axis about which the transmitter housing is rotatable.

20. The implantable hearing aid system according to claim 15, wherein the transmitter connector is tiltably detachable from the interface connector.

* * * * *